(12) United States Patent
Lett et al.

(10) Patent No.: US 11,980,528 B2
(45) Date of Patent: May 14, 2024

(54) WOUND CLOSURE SYSTEM

(71) Applicants: Hunter Scott Lett, Auburn, AL (US);
Ricky L. Ledkins, Dadeville, AL (US)

(72) Inventors: Hunter Scott Lett, Auburn, AL (US);
Ricky L. Ledkins, Dadeville, AL (US)

( * ) Notice: Subject to any disclaimer, the term of this patent is extended or adjusted under 35 U.S.C. 154(b) by 622 days.

(21) Appl. No.: 16/752,300

(22) Filed: Jan. 24, 2020

(65) Prior Publication Data
US 2021/0228415 A1    Jul. 29, 2021

(51) Int. Cl.
*A61F 13/00*    (2006.01)
*A61F 13/02*    (2006.01)

(52) U.S. Cl.
CPC .... *A61F 13/00* (2013.01); *A61F 2013/00468* (2013.01); *A61F 2013/00561* (2013.01); *A61F 2013/00565* (2013.01); *A61F 2013/00655* (2013.01); *A61F 13/0266* (2013.01)

(58) Field of Classification Search
CPC ............... A61F 13/00; A61F 13/00021; A61F 13/0008; A61F 13/023; A61F 13/0233; A61F 13/0253; A61F 13/60; A61F 13/00085; A61F 13/0266; A61F 13/0259; A61F 13/0236; A61F 13/0246; A61F 2013/00089; A61F 2013/00289; A61F 2013/00468; A61F 2013/00561; A61F 2013/00565; A61F 2013/0057; A61F 2013/00655; A61F 2013/00582; A61F 15/00; A61F 15/006; A61F 15/008; A61M 35/00; A61L 15/00; A61L 15/58; A61L 26/00

USPC ............. 602/41–43, 52–54, 57–58, 78; 128/887–893; 604/304, 307; 424/445, 424/448
See application file for complete search history.

(56) References Cited

U.S. PATENT DOCUMENTS

| | | | | |
|---|---|---|---|---|
| 4,531,521 A * | 7/1985 | Haverstock | .......... | A61B 17/085 606/215 |
| 4,881,546 A * | 11/1989 | Kaessmann | .......... | A61B 17/085 606/217 |
| 5,263,970 A * | 11/1993 | Preller | .......... | A61F 13/023 602/58 |
| 5,336,219 A * | 8/1994 | Krantz | .......... | A61B 17/085 606/213 |
| 5,377,695 A * | 1/1995 | An Haack | .......... | A61B 17/085 606/217 |

(Continued)

FOREIGN PATENT DOCUMENTS

WO    2017039677 A1    3/2017

*Primary Examiner* — Caitlin A Carreiro
(74) *Attorney, Agent, or Firm* — Bradley Arant Boult Cummings LLP; Rudy Hill; Lucas R. Yordy

(57) ABSTRACT

A wound closure includes one or more bandages. The one or more bandages include a first bandage and a second bandage. Each of the first bandage and the second bandage include a skin attachment portion having a skin fastener for attaching the bandages to a subject. Each of the first bandage and the second bandage include a closure portion having a closure fastener for attaching the closure portions with one another. The skin fastener and closure fastener may include an adhesive. The bandages may include a leg for folding over, and attaching to, the attached closure portions to form a secured folded closure. The secured folded closure may be folded generally flat against, and secured with, one of the skin attachment portions.

18 Claims, 8 Drawing Sheets

(56) References Cited

U.S. PATENT DOCUMENTS

| | | | | |
|---|---|---|---|---|
| 5,415,626 A | * | 5/1995 | Goodman | A61F 13/025 |
| | | | | 602/41 |
| 6,899,104 B1 | | 5/2005 | Inman et al. | |
| 7,597,706 B2 | | 10/2009 | Kanner et al. | |
| 7,696,399 B2 | * | 4/2010 | Rogers | A61F 13/025 |
| | | | | 602/57 |
| 8,764,792 B2 | * | 7/2014 | Weiser | A61B 17/085 |
| | | | | 602/42 |
| 2009/0240186 A1 | * | 9/2009 | Fang | A61B 17/085 |
| | | | | 602/54 |
| 2014/0088620 A1 | | 3/2014 | Tobias | |

\* cited by examiner

WOUND CLOSURE SYSTEM

TECHNICAL FIELD

The present disclosure relates to a bandage for wounds. More specifically, the disclosure is directed towards a wound closure system having one or more bandages for pulling together edges of a wound for healing.

BACKGROUND OF INVENTION

Wound closures are commonly employed to close wounds and assist wounds in healing. Such wounds include cuts and lacerations as well as incisions, such as incisions performed during medical procedures. However, these mechanical closures can interfere with wound healing and lead to increased scaring and longer heal times for subjects. Moreover, these closures fail to protect the wound and immediately surrounding sites from mechanical forces or contamination (e.g., contact with bacteria), and do not absorb any discharge (e.g., blood) from the wound. Therefore, often dressings are required to supplement these closures. Furthermore, sutures, staples, and surgical glue must be applied by skilled medical practitioners, making them more expensive and less convenient to use, as well as difficult to change or replace as the wound heals. While bandages have been developed that partially hold closed wounds (i.e., butterfly closures), these bandages fail to be effective for larger and deeper wounds, such as those associated with surgical incisions.

Thus, a need exists for bandages that can mechanically hold closed and protect wounds of varying lengths, while being convenient to use and easily removable or replaceable.

BRIEF SUMMARY

In one aspect, wound closure system includes a first bandage and a second bandage. Each of the first bandage and the second bandage include a skin attachment portion having a skin fastener, such as an adhesive, disposed thereon and a closure portion. The first bandage and the second bandage may be elongated. The closure portion of the first bandage or the closure portion of the second bandage includes a closure fastener. Both of the closure portion of the first bandage and the closure portion of the second bandage may include the closure fastener. The closure fastener may be a zipper or an adhesive. The skin fastener or the closure fastener may include a removable, non-adhesive layer.

The first bandage and the second bandage may be flexible. The first bandage and the second bandage may be configured to fold along an axis between the skin attachment portion and the closure portion.

The first bandage or the second bandage may include a leg extending from the closure portion opposite of the skin attachment portion. The leg may include a fastener, such as an adhesive. The first bandage and the second bandage each may include a bottom face and a top face. The adhesive may be disposed on the bottom face of each of the first bandage and the second bandage. At least one of the top face of the skin attachment portion of the second bandage, the top face of the skin attachment portion of the first bandage, or the top face of the leg of the first bandage may include an adhesive.

In another aspect, a method of treating a wound of a subject is disclosed. The method includes providing a wound closure system that includes a first bandage and a second bandage. Each of the first bandage and the second bandage include a skin attachment portion having a skin fastener, such as an adhesive, disposed thereon and a closure portion. The skin fastener of the skin attachment portion may include a removable, non-adhesive layer. The first bandage and the second bandage may be elongated. The closure portion of the first bandage or the closure portion of the second bandage includes a closure fastener. The closure fastener may be an adhesive, which may include a removable, non-adhesive layer. Both of the closure portion of the first bandage and the closure portion of the second bandage may include the closure fastener. The method includes attaching the first bandage to a first skin site proximate to the wound via the skin fastener. The method includes attaching the second bandage to a second skin site proximate to the wound via the skin fastener. The method includes fastening closure portions of the adhered first bandage and the adhered second bandage with the closure fastener to a closed position.

The method may include moving the attached first bandage and the attached second bandage toward one another before the fastening of the closure portions. Each of the first bandage and the second bandage may include a fold between the skin attachment portion and the closure portion. Each of closure portions of the first bandage and the second bandage may be folded to extend away from the subject before the fastening of the closure fastener. Each of the first bandage and the second bandage may be flexible and configured to fold along an axis disposed between the skin attachment portion and the closure portion. The method may include folding each of closure portions of the first bandage and the second bandage to extend away from the subject before the fastening of the closure portions.

The wound may be elongated, and each of the first bandage and the second bandage may be elongated. The wound may have a wound length, and the first bandage and the second bandage may each have a bandage length that is about equal to, or greater than, the wound length.

The first bandage may include a leg extending from the closure portion in a direction opposite of the skin attachment portion. The leg may comprise a leg fastener, such as an adhesive. The method may include folding the leg of the first bandage on the fastened closure portions. The method may include adhering the folded extended closure portion with the fastened closure portion via the leg fastener to form a secured folded closure. The method may include folding the secured folded closure on the skin attachment portion of the first bandage or the second bandage to form a generally flat and closed wound closure system. The method may include attaching, or adhering, the secured folded closure with the skin attachment portion of the first bandage or the second bandage via a leg closure.

BRIEF DESCRIPTION OF DRAWINGS

It should be noted that identical features in different drawings are shown with the same reference numeral.

DETAILED DESCRIPTION

Figure 1:
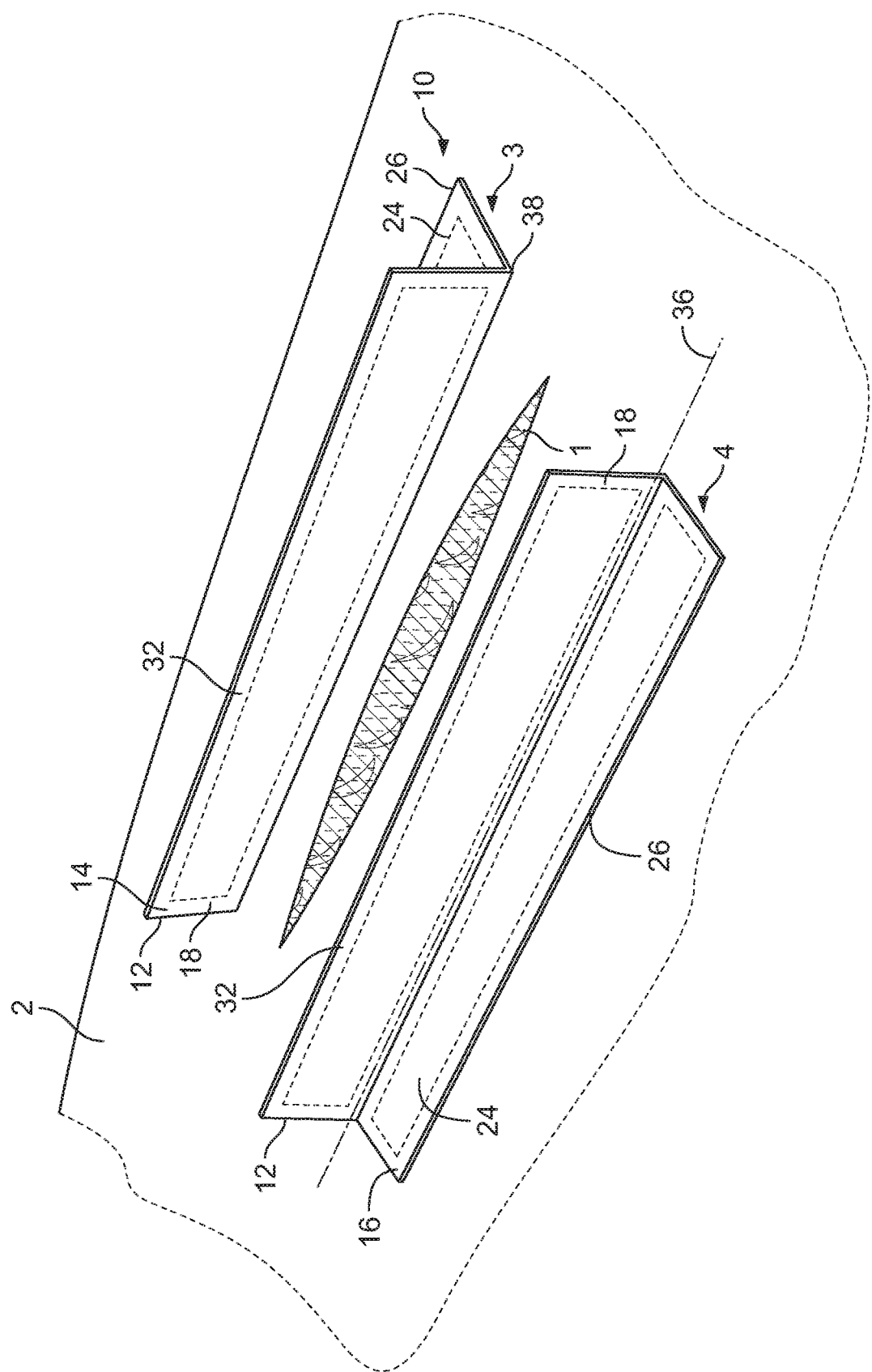
FIG. 1 shows a front perspective view of an embodiment of a wound closure system on a subject.
Figure 2A:
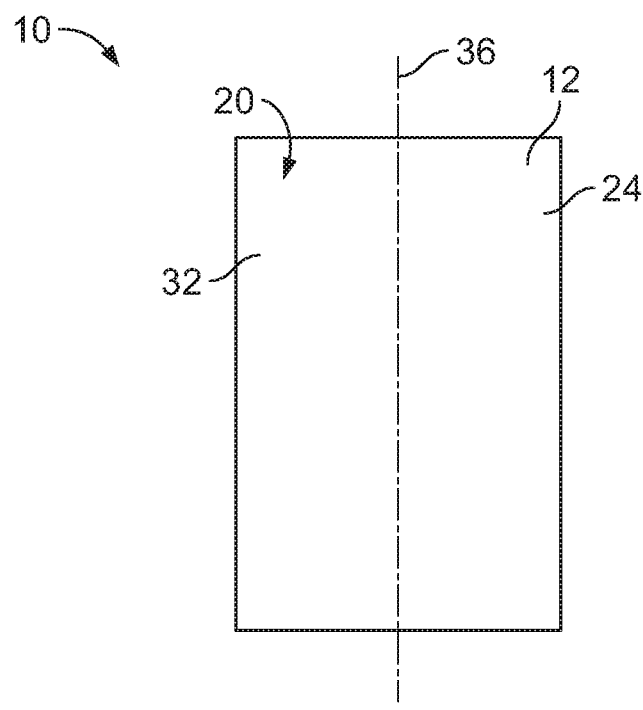
FIG. 2A shows a front elevation view of a bandage according to an embodiment of the wound closure system.
Figure 2B:
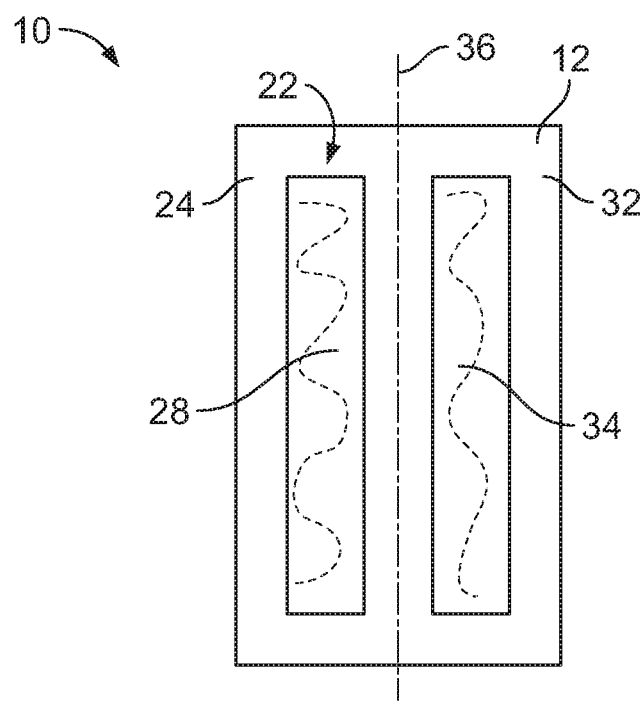
FIG. 2B shows a rear elevation view of a bandage according to an embodiment of the wound closure system.
Figure 3:
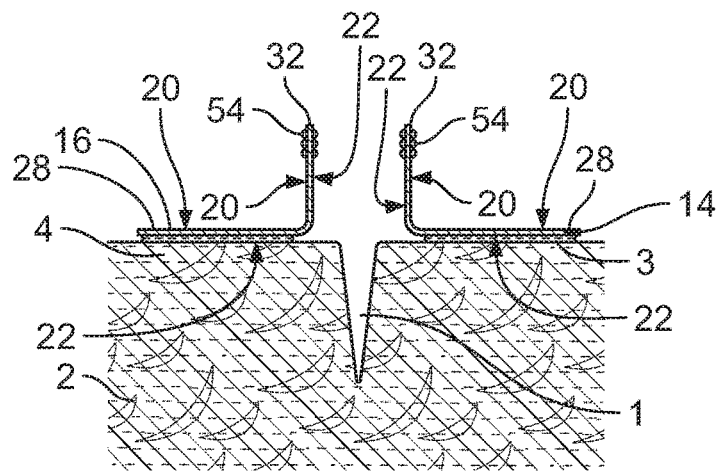
FIG. 3 shows a cross-sectional view of an embodiment of the wound closure system on a subject.
Figure 4:
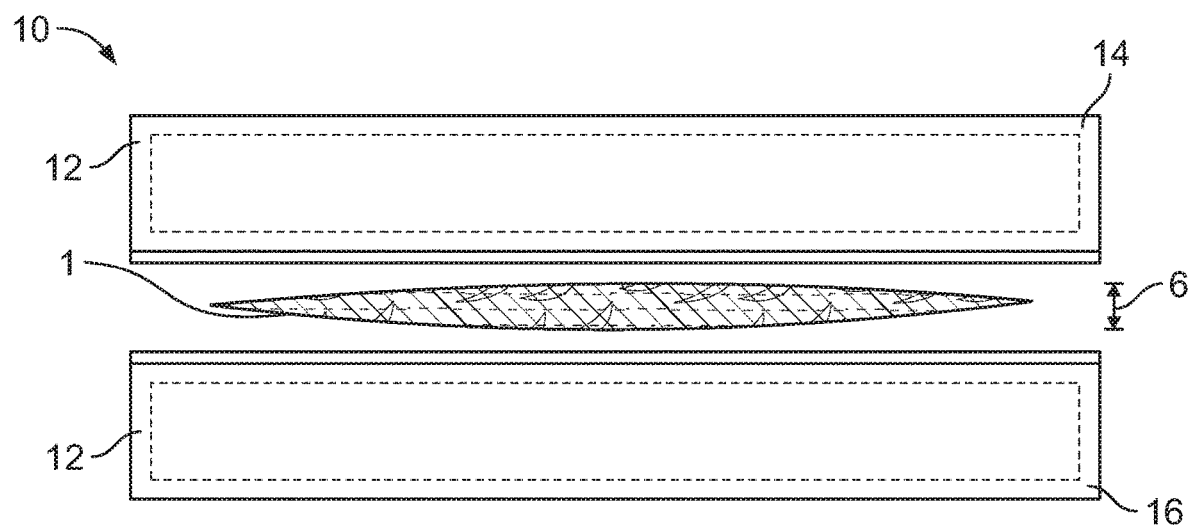
FIG. 4 shows a top view of the embodiment of the wound closure system of FIG. 3.

Reference now will be made in detail to the embodiments of the present disclosure. It will be apparent to those of ordinary skill in the art that various modifications and variations can be made to the teachings of the present disclosure without departing from the scope of the disclosure. For instance, features illustrated or described as part of one embodiment can be used with another embodiment to yield a further embodiment.

Thus, it is intended that the present disclosure covers such modifications and variations that come within the scope of the appended claims and their equivalents. Other objects, features, and aspects of the present disclosure are disclosed in or are apparent from the following description. It is to be understood by one of ordinary skill in the art that the present disclosure is a description of exemplary embodiments only and is not intended as limiting the broader aspects of the present disclosure.

The terms "individual," "subject," or "patient" as used herein refer to any animal, including mammals, such as mice, rats, other rodents, rabbits, dogs, cats, swine, cattle, sheep, horses, or primates, and humans. The term may specify male or female or both, or exclude male or female.

For the sake of clarity, not all reference numerals are necessarily present in each drawing Figure. In addition, positional terms such as "upper," "lower," "side," "top," "bottom," "vertical," "horizontal," etc. refer to the wound closure system when in the orientation shown in the drawings. The skilled artisan will recognize that the wound closure system can assume different orientations when in use.

Referring to FIGS. 1-10D, a wound closure system 10 has been developed. The wound closure system 10 is intended to cover and hold closed a wound 1 of a subject 2. The wound closure system 10 may cover at least part of, or the entirety of, the wound 1. The wound 1 may be a skin wound, such as, for example, a laceration, an incision (e.g., a surgical incision), a burn, an infection, a scrape, a bruise, or a scratch. The wound closure system 10 includes one or more bandages 12, such as a first bandage 14 and a second bandage 16. As used herein, the term "dressing" is interchangeable with and equivalent to the term "bandage." While not shown, it should be understood that the one or more bandages 12 may include any number of bandages or dressings (e.g., a third, a fourth, or a fifth bandages), each which may comprise, or lack, any of the features discussed for any of the bandages herein.

The one or more bandages 12 may be provided in separate form or may be attached. In embodiments where the bandages 12 are provided in separate form, an advantage is that the bandages 12 may be conveniently and independently positioned and secured on the subject 2. The one or more bandages 12 may be dimensioned to extend at least partially, or completely, along the wound 1. The one or more bandages 12 may be elongated. The elongated one or more bandages 12 are advantageous for wounds 1 that are elongated, which is especially the case with wounds 1 that are lacerations and incisions. In some embodiments, the one or more bandages 12 may have a length 13 that is about equal to, or greater than, a wound length 5 of the wound 1.

The one or more bandages 12 may include a body 18. The body 18 may be constructed of any suitable material. Exemplary suitable materials of the body 18 include fabric (e.g., cotton or polyester), polymers (e.g., polyvinyl chloride, polyethylene, polyurethane), or latex. The body 18 may be flexible or rigid. The body 18 may comprise a top face 20 and a bottom face 22. As used herein, the "bottom face" may be described as the face, or surface, of the bandages 12 that is configured to at least partially face the wound 1, and the "top face" may be described as the face, or surface, of the bandages 12 that is configured to at least partially face away from the wound 1 when the bandages 12 are in-use.

The first bandage 14 may be configured to attach to the first skin site 3 and the second bandage 16 may be configured to attach to the second skin site 4. In embodiments having more than two bandages 12, each additional bandage 12 may attach to the corresponding skin site 3, 4. The skin sites 3, 4 may be around the wound 1, such as generally on opposite sides of the wound 1. In some embodiments, the wound 1 is elongated, and the skin sites 3, 4 are on each of the elongated sides of the wound 1.

The one or more bandages 12 may include a skin attachment portion 24 disposed at a skin attachment side 26 of the bandages 12. The skin attachment portion 24 may include a skin fastener 28, such as adhesive or tape, for releasably securing the skin attachment portion 24 on a corresponding first skin site 3 and a second skin site 4 that are proximate to the wound 1. As used herein, a "skin fastener" may be any fastener that is suitable for attaching bandages 12 to skin, such as tape, adhesive, gum, and the like. Examples of suitable skin fasteners include acrylates, such as methacrylates and epoxy diacrylates. In this way, the one or more bandages 12 may be described as being "self-adhesive." Also, any "fastener" disclosed herein may be releasable or reattachable.

Any fastener or closure discussed herein, such as skin fastener 28, may include a removable, non-adhesive outer surface layer 30 (i.e., a backing) so that the one or more bandages 12 can be more conveniently handled (e.g., without contacting adhesive), and once the one or more bandages 12 are to be secured to the subject 2, the outer surface layer 30 may be removed, exposing the fastener or closure for contact with the intended substrate (e.g., skin sites 3, 4 of the subject 2). The fasteners and closures described herein may be of any relative size (e.g., on all, on most of, on some of, or on at least part of) the one or more bandages and in any shape or profile (e.g., rectangular, circular, oval, and/or lines whether straight or curved).

The one or more bandages 12 may comprise a closure portion 32. The closure portion 32 may be proximate to the skin attachment portion 24 on the body 18. The closure portion 32 may be described as the portion of each of the one or more bandages 12 that is configured to attach with, or receive, another of the one or more bandages 12. By way of example, the closure portion 32 of the first bandage 14 may be configured for attachment with the closure portion 32 of the second bandage 16. The closure portion 32 may comprise a closure fastener 34, such as a zipper, a tie, a hook and loop fastener, an adhesive, a tape, or any other suitable closure. In embodiments of the system 10 where the closure fastener 34 includes a cooperative closure (e.g., a zipper or a hook and loop fastener), each closure fastener 34 of the one or more bandages 12 may include a cooperative part of the cooperative closure. Other examples of suitable closure fasteners 34 include acrylates, such as methacrylates and epoxy diacrylates. The closure fastener 34 may include the removable, non-adhesive outer surface layer 30. The closure portion 32 may not be in direct contact with the wound 1 when the system is in use, which is beneficial for healing and subject comfort.

The one or more bandages 12 may be configured to fold. As used herein, the word "fold" also includes bend and means that the bandage 12 is deformable along a plane, unless otherwise stated or is clear from context. The one or more bandages 12 may fold along a closure axis 36 that is disposed between, or proximate to, the skin attachment portion 24 and the closure portion 32. The closure axis 36 may extend lengthwise along the body 18. The body 18 may be one or more of weaker, thinner, or perforated along the closure axis 36 such that the body 18 may easily fold along the closure axis 36. The body 18 may have a fold 38, also which may be described as a crease, preformed along the closure axis 36. Beneficially, the fold feature allows the closure portion 32 and the skin attachment portion 24 to pivot relative to one another.

Figure 5A:
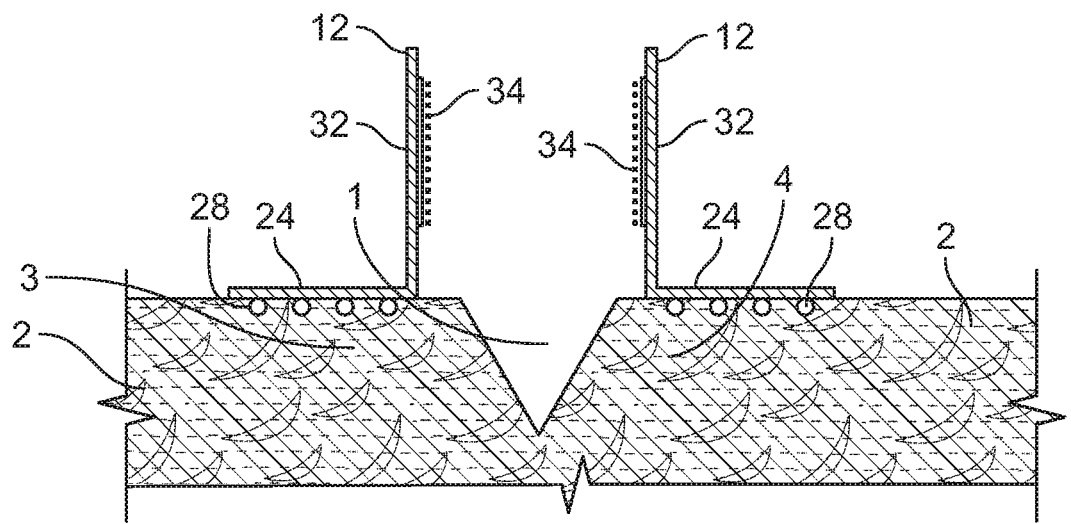
FIG. 5A shows a cross-sectional view of another embodiment of the wound closure system in an open position.
Figure 5B:
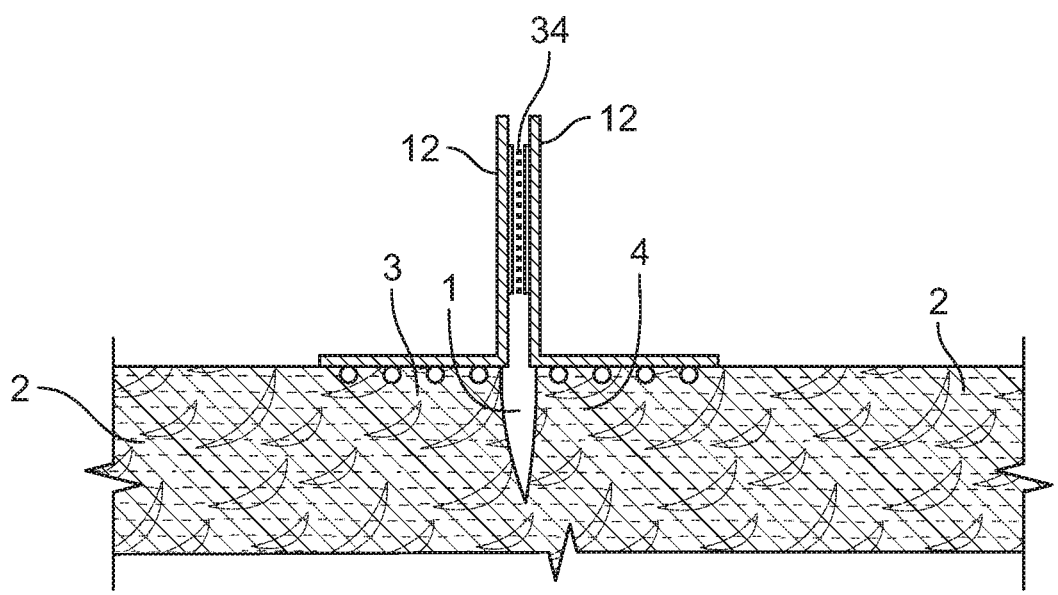
FIG. 5B shows a cross-sectional view of the embodiment of the wound closure system of FIG. 5A in a joined position.
Figure 6:
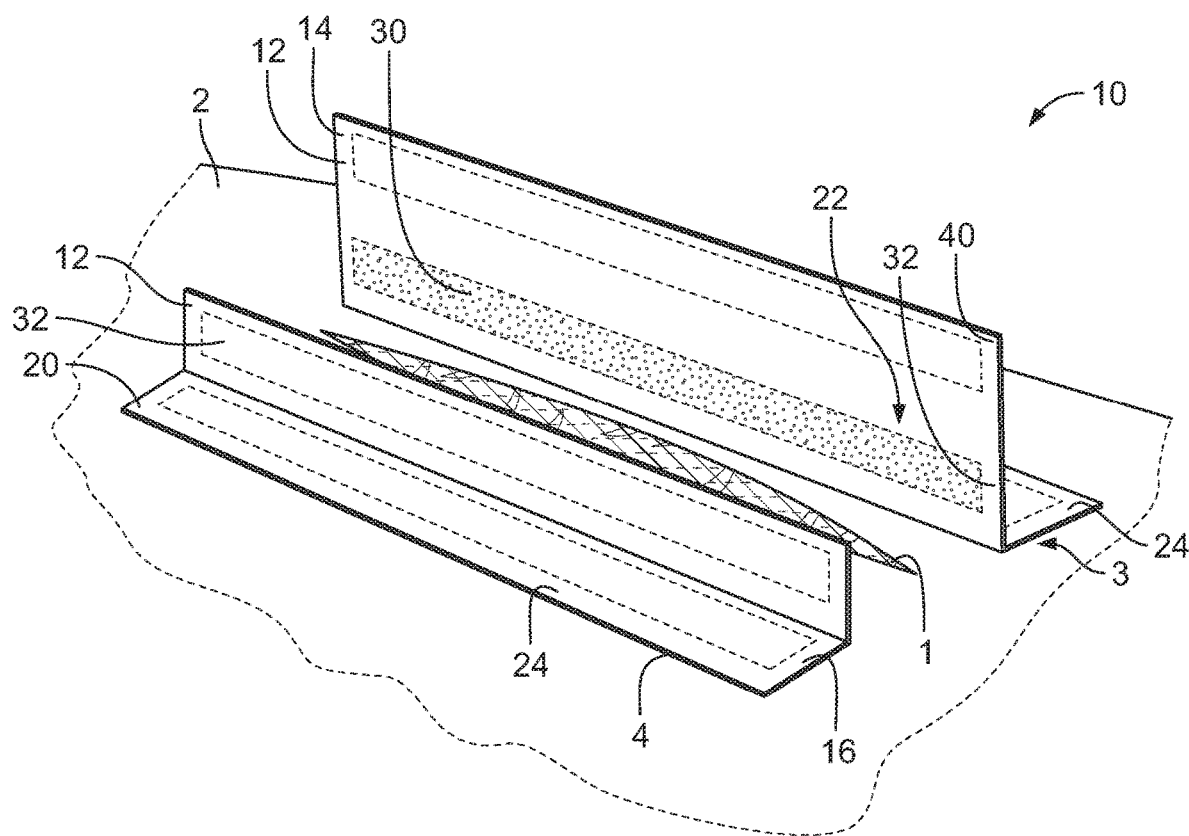
FIG. 6 shows a front perspective view of another embodiment of a wound closure system on a subject.
Figure 7:
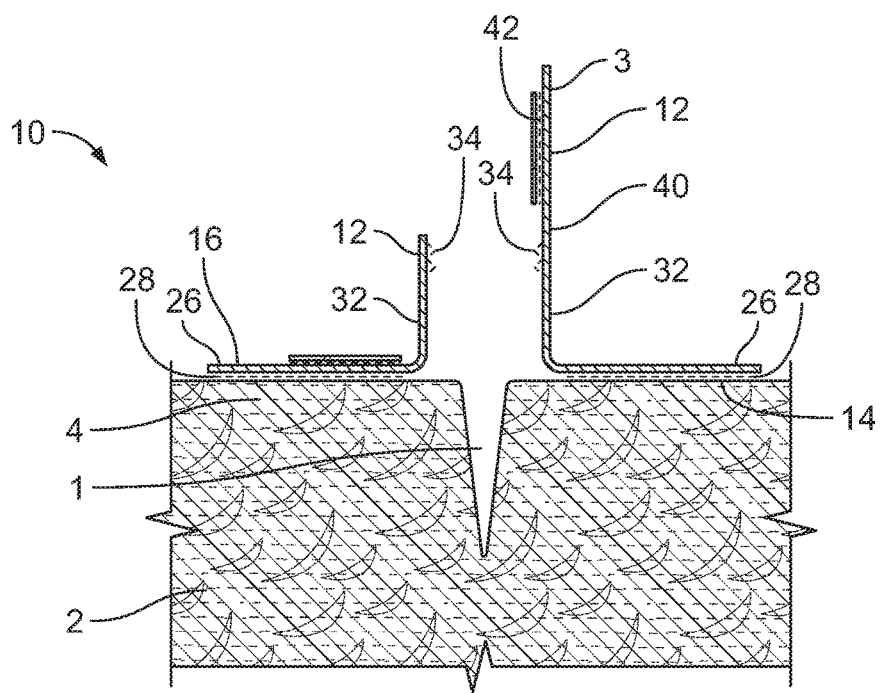
FIG. 7 shows a cross-sectional view of the embodiment of the wound closure system of FIG. 6.
Figure 8A:
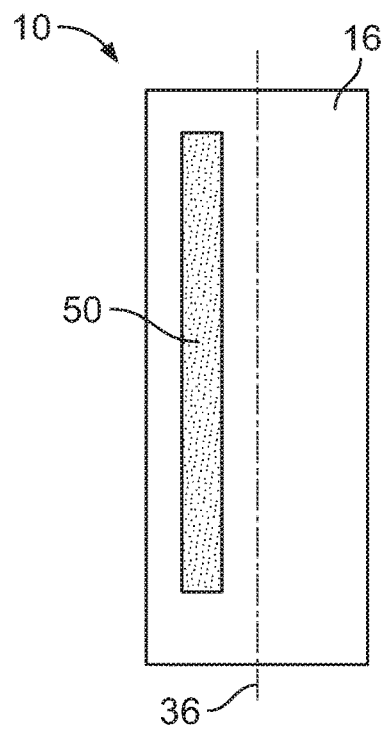
FIG. 8A shows a front elevation view of a bandage according to one embodiment of the wound closure system.
Figure 8B:
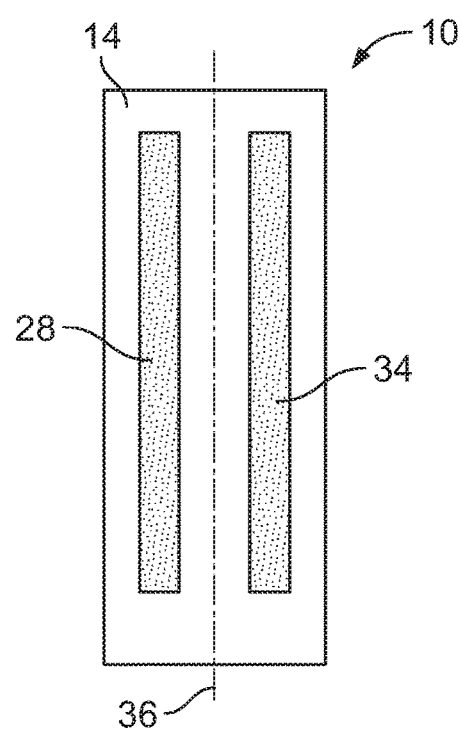
FIG. 8B shows a rear elevation view of the bandage of FIG. 8A.
Figure 8C:
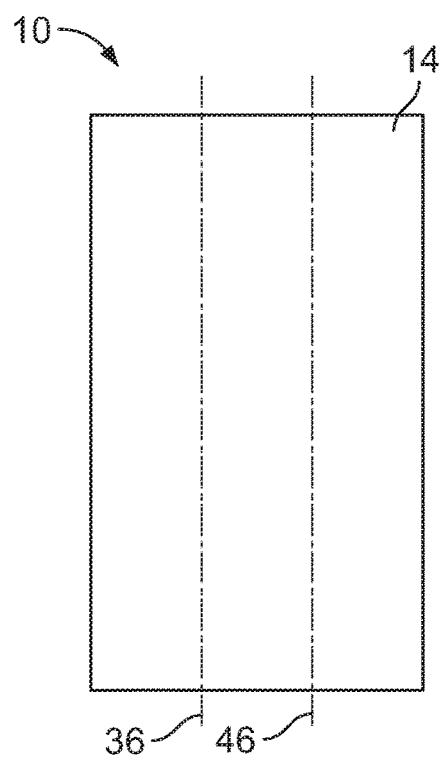
FIG. 8C shows a front elevation view of a bandage having a leg according to an embodiment of the wound closure system.
Figure 8D:
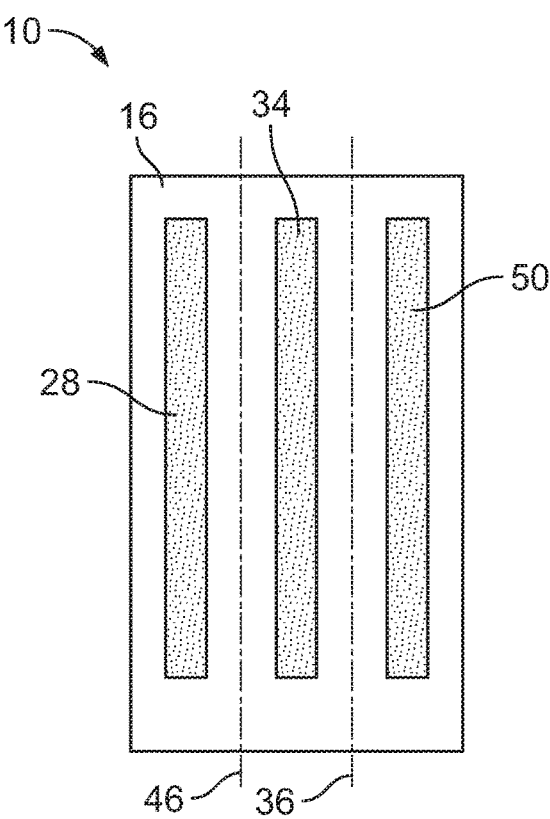
FIG. 8D shows a rear elevation view of the bandage of FIG. 8C.
Figure 9:
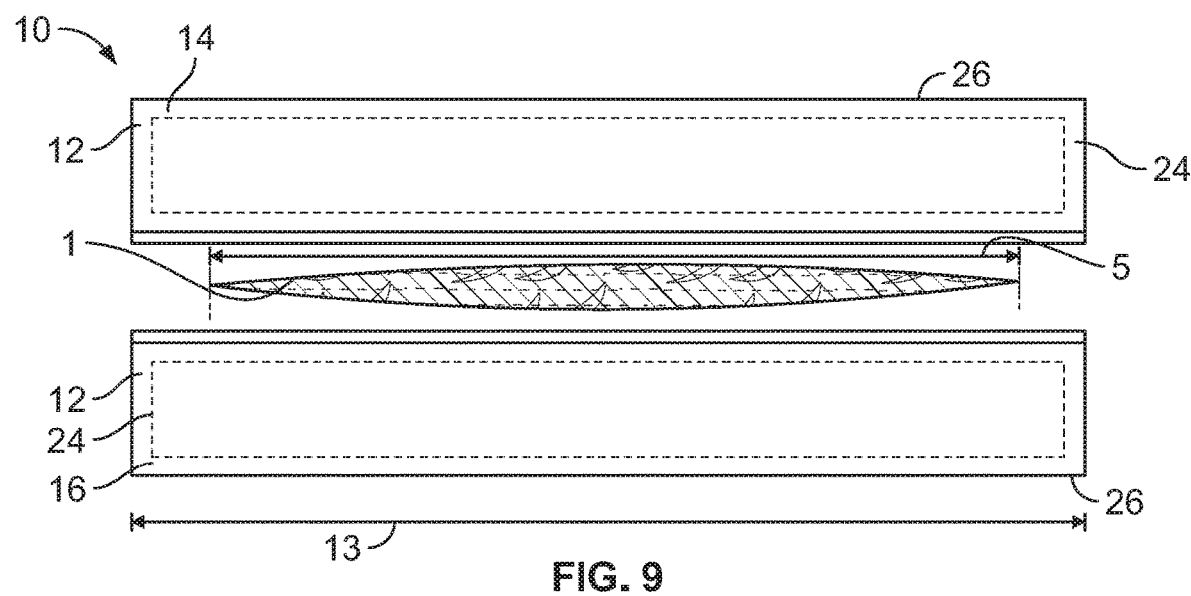
FIG. 9 shows a top view of the embodiment of the wound closure system of FIG. 7.
Figure 10A:
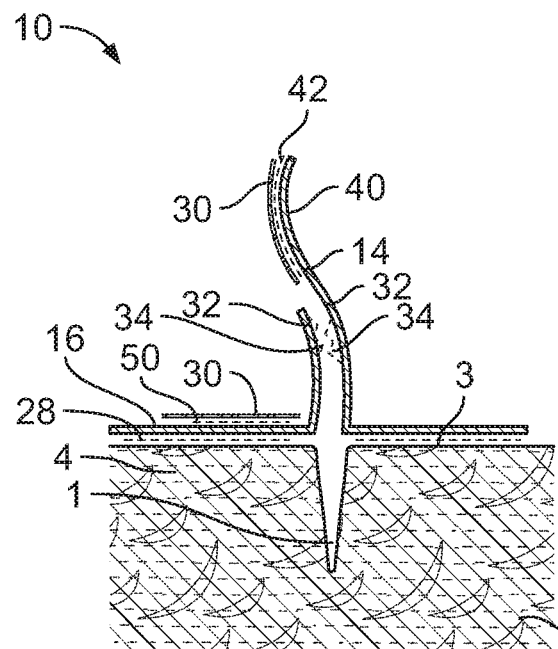
FIG. 10A shows a cross-sectional view of an embodiment of the wound closure system in an open position.
Figure 10B:
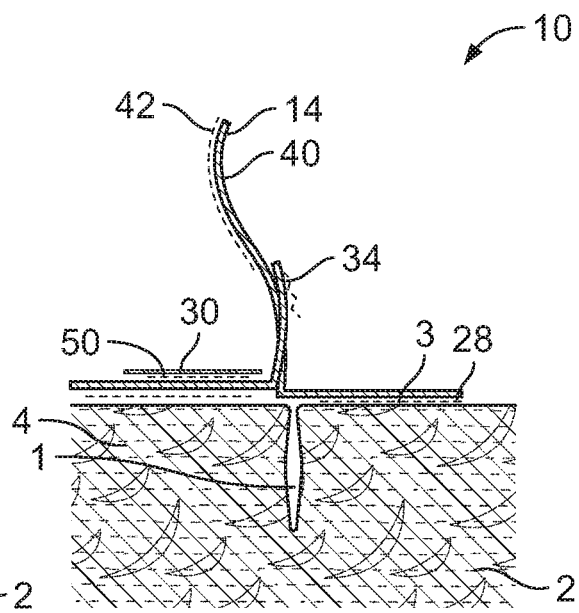
FIG. 10B shows a cross-sectional view of the embodiment of the wound closure system of FIG. 10A in a joined position.

This fold feature is especially advantageous when the skin attachment portion 24 is fastened via the skin fastener 28, as the closure portion 32 may pivot along the axis 36 while the skin attachment portion 24 is fastened to the subject 2 (i.e., one of the skin sites 3, 4) so that the closure portions 32 of two or more bandages 12 may pivot and attach together via the closure fastener 34 to a closed or joined position, as shown in FIGS. 5B and 10B. This allows the one or more bandages 12 to push (or pull) the skin located at the skin sites 3, 4 toward each other, thereby pushing (or pulling) closed the wound 1. It is believed that by reducing a width 6 of the wound 1 in this manner by pushing or pulling the edges of the wound together via the system 10, the wound 1 will heal faster and more completely, and any associated scarring will be reduced or prevented.

The one or more bandages 12 may fold, or bend, such that joined closure portions 32 may pivot downwardly on the skin attachment portion 24. The one or more bandages 12 may include a top face fastener 54 disposed on the top face 20 of the closure portion 32 or the top face 20 of the skin attachment portion 24, such as a zipper, a tie, an adhesive, a tape, a hook and loop fastener, or any other suitable fastener. The top face fastener 54 may extend lengthwise along the body 18.

As shown in FIGS. 6-10D, the one or more bandages 12 may include a leg 40 that extends from the closure 32, thereby functioning as an extension of the closure portion 32 that extends opposite on the body 18 from the skin attachment portion 24. The leg 40 may include a leg fastener 42, such as a zipper, a tie, an adhesive, a tape, a hook and loop fastener, or any other suitable fastener. The leg fastener 42 may be disposed on the bottom face 22 proximate to the closure fastener 34. The leg fastener 42 and the closure fastener 34 may extend lengthwise along the body 18. The leg fastener 42 and the closure fastener 34 may extend parallel to one another and the length of the wound 1.

The one or more bandages 12 may fold along a leg axis 44 that is disposed between, or proximate to, the leg 40 and the closure portion 32. The leg axis 44 may extend lengthwise along the body 18. The body 18 may be one or more of weaker, thinner, or perforated along the leg axis 44 such that the body 18 may easily fold along the leg axis 44. The body 18 may have a leg bend 46, also which may be described as a crease, preformed along the leg axis 44. Advantageously, the leg fold feature allows the leg 40 and the closure portion 32 to pivot relative to one another. This feature is especially advantageous after the one or more bandages 12 are attached to the subject 2. Indeed, after the closure portions 32 of the one or more bandages 12 are fastened to one another, the leg 40 may pivot around the leg axis 44 and thus extend downwardly over the fastened closure portions 32. The leg 40 may be secured over the fastened closure portions 32 via the leg fastener 42 to form a secured folded closure 48. The leg fastener 42 may be disposed on the bottom surface face 22 of the leg 40, on the top face 20 of the closure portion 32, or both. In this way, the leg 40 provides an additional area of attachment to the one or more bandages 12, providing further strength to the system 10.

The one or more bandages 12 may be impregnated with, or include, an active ingredient configured to contact the subject 2 when the bandages 12 are in use. Such active ingredients include antibiotics, such as bacitracin, cortisporin, erythromycin, gentamicin, mafernide, mupircin, neomycin, ozenoxacin, reapamulin, and silver sulfadiazine, steroids such as hydrocortisone, desonide, fluocinolone acetonide, triamcinolone acetonide, and alclometasone dipropionate, or antifungals. The active ingredient may be included an amount effective to deliver an effective amount of the active ingredient.

The one or more bandages 12 may comprise one or more pads (not shown) disposed on the bottom face 22 to absorb discharge from the wound (e.g., blood). The one or more pads may include a non-stick layer or coating and may be constructed of any suitable material (i.e., cotton).

Figure 10C:
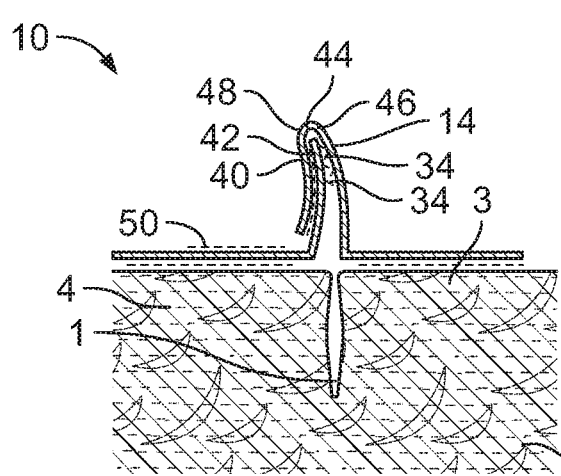
FIG. 10C shows a cross-sectional view of the embodiment of the wound closure system of FIG. 10A in a closed position.
Figure 10D:
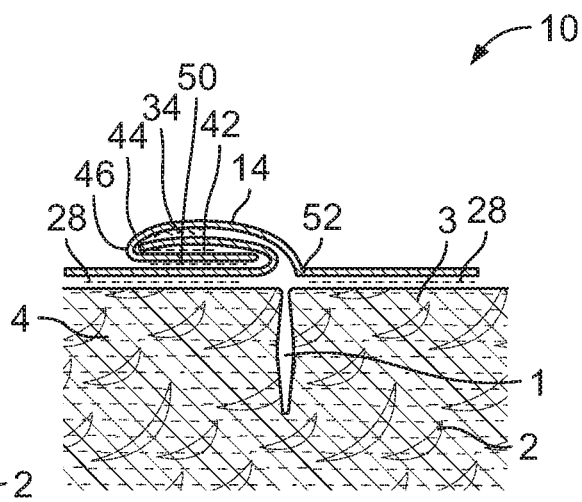
FIG. 10D shows a cross-sectional view of the embodiment of the wound closure system of FIG. 10A secured in a flat position.

The secured folded closure 48 may be configured to bend, or fold, onto the skin attachment portion 24 of the one or more bandages 12. The secured folded closure 48 may fasten with the skin attachment portion 24 via a leg closure 50, such as a zipper, a tie, an adhesive, a tape, a hook and loop fastener, or any other suitable fastener. The leg closure 50 may be disposed on one or more of the top face 20 of the leg 40 or the top face 20 of the skin attachment portion 24. When the leg 40 and the skin attachment portion 24 are in a disengaged position, as shown in FIG. 10C, the secured folded closure 48 is generally upright. When the leg 40 and the skin attachment portion 24 are in an engaged (i.e., fastened or attached) position via the leg closure 50, as shown in FIG. 10D, the leg 40 and the skin attachment portion 24 are generally against the subject 2, thereby forming a generally flat and closed wound closure system 10. Advantageously, the flat and closed wound closure system 10 is mechanically secure in holding the lateral edges of the wound 1 together (benefits of which are discussed, above) while being comfortable and unobtrusive for the subject 2.

Methods of using any of the embodiments of the wound closure system 10 are provided for, for example, healing wounds 1, treating wounds 1, promoting the healing of wounds 1, preventing or reducing scaring from wounds 1, and reducing healing time in wounds 1, for the subject(s) 2 having such wounds 1 or who are in need thereof. It shall be understood that unless otherwise stated or is clear from context, the steps of the disclosed methods may be performed in any order.

The method may include providing the wound system 10, or components thereof, such as the one or more bandages 12. The method may include attaching (e.g., fastening or adhering) the first bandage 14 and the second bandage 16 to the first skin site 3 and the second skin site 4, respectively. As discussed above, the skin sites 3, 4 may be proximate to the wound 1 and generally opposite one another across the wound 1.

The method includes fastening closure portions 32 of the attached bandages 14, 16 to one another via the closure fastener 34 to a closed position. The method may include moving the attached (e.g., fastened or adhered) bandages 14, 16 toward one another, thereby moving the edges of the wound 1 closer to one another. This moving may be performed before the bandages 14, 16 are attached to one another.

The method may include folding, or bending, the closure portions 32 of the bandages 14, 16 along the axis 36 so that they are generally orthogonal to the skin attachment portions 24 of the bandages 14, 16. This folding, or bending, may be performed before the closure portions 32 are attached to one another and after the skin attachments portions 24 are attached to the subject 2.

The method may include folding, or bending, the leg 40 of the one or more bandages 12 onto the generally orthogonal closure portions 32, such as along the leg axis 44. The leg 40 may be attached to the closure portions 32 in the folded or bent position via the leg fastener 42 to form the secured folded closure 48.

The method may include folded, or bending, the secured folded closure 48 on the skin attachment portion 24 (e.g., on the top face 20) and attaching (e.g., fastening or adhering) the secured folded closure 48 to the skin attachment portion 24 along a secured folded closure axis 52 to form the wound closure system 10 that is generally flat and closed to the external environment while pushing (or pulling) edges of the wound 1 together.

The methods and systems 10 described herein may be performed on the wound 1 that has been sutured, glued, stapled, otherwise closed to take a mechanical load from the suture, glue, staple(s), or closure. Such use may be especially advantageous when dissolvable (including resorbable) sutures or glues are employed, as the system 10 bears the lateral mechanical load as the sutures or glues dissolve and lose their mechanical strength.

Although embodiments of the disclosure have been described using specific terms, devices, and methods, such description is for illustrative purposes only. The words are words of description rather than of limitation. It is to be understood that changes and variations may be made by those of ordinary skill in the art without departing from the spirit or scope of the present disclosure, which is set forth in the following claims. It is further noted that any range provided herein provides support and a basis for any subset within that range. Further embodiments of the disclosure contain combinations, or exclusions, of different embodiments described herein.

Thus, although there have been described embodiments of the present invention of a new and useful wound closure system 10, it is not intended that such references be construed as limitations upon the scope of this invention except as set forth in the following claims.

What is claimed is:

1. A method of treating a wound of a subject, comprising:
   providing a wound closure system including a first bandage and a second bandage, each of the first bandage and the second bandage including a skin attachment portion,
   a skin fastener disposed on the skin attachment portion, and
   a closure portion, wherein the closure portion of the first bandage is configured to attach directly to the closure portion of the second bandage and wherein at least one of the closure portion of the first bandage or the closure portion of the second bandage includes a closure adhesive,
   wherein the first bandage comprises a leg including a leg adhesive, the leg attached to the closure portion opposite of the skin attachment portion,
   wherein the first bandage is configured to fold at a leg axis disposed between the leg and the closure portion of the first bandage to allow the leg to extend downwardly over and secure to the closure portion of the second bandage;
   attaching the first bandage to a first skin site proximate to the wound via the skin fastener;
   attaching the second bandage to a second skin site proximate to the wound via the skin fastener; and
   fastening the closure portions of the attached first bandage and the attached second bandage with the closure adhesive to a closed position.

2. The method of claim 1, further comprising folding the leg of the first bandage on the fastened closure portions.

3. The method of claim 2, further comprising adhering the folded leg of the first bandage with the fastened closure portions to form a secured folded closure.

4. The method of claim 3, further comprising folding the secured folded closure on the skin attachment portion of the first bandage or the second bandage to form a generally flat and closed wound closure system.

5. The method of claim 4, further comprising adhering the secured folded closure with the skin attachment portion of the first bandage or the second bandage.

6. The method of claim 1, wherein each of the skin fasteners comprise a skin adhesive.

7. The method of claim 6, wherein the skin adhesive of each of the skin fasteners comprise a removable, non-adhesive layer.

8. The method of claim 1, further comprising moving the attached first bandage and the attached second bandage toward one another before the fastening of the closure portions.

9. The method of claim 1, wherein each of the first bandage and the second bandage are flexible and configured to fold along an axis disposed between the skin attachment portion and the closure portion, and wherein the method includes folding the closure portions of the first bandage and the second bandage to extend away from the subject before fastening.

10. The method of claim 1, wherein the wound is elongated, and each of the first bandage and the second bandage are elongated.

11. The method of claim 1, wherein each of the first and second bandages are dimensioned to cover the wound.

12. A wound closure system, comprising:
a first bandage and a second bandage, each of the first bandage and the second bandage including
a skin attachment portion,
a skin fastener disposed on the skin attachment portion, and
a closure portion, wherein the closure portion of the first bandage is configured to attach directly to the closure portion of the second bandage and wherein at least one of the closure portion of the first bandage or the closure portion of the second bandage includes a closure adhesive,
wherein the first bandage comprises a leg including a leg adhesive, the leg attached to the closure portion opposite of the skin attachment portion,
wherein the first bandage is configured to fold at a leg axis disposed between the leg and the closure portion of the first bandage to allow the leg to extend downwardly over and secure to the closure portion of the second bandage.

13. The wound closure system of claim 12, wherein each of the skin fasteners comprise a skin adhesive.

14. The wound closure system of claim 13, wherein each of the skin adhesives includes a removable, non-adhesive layer.

15. The wound closure system of claim 12, wherein the closure portion of the first bandage and the closure portion of the second bandage each include the closure adhesive.

16. The wound closure system of claim 12, wherein each of the first bandage and the second bandage are elongated.

17. The wound closure system of claim 12, wherein each of the first bandage and the second bandage are flexible and configured to fold along an axis between the skin attachment portion and the closure portion.

18. The wound closure system of claim 12, wherein the first bandage and the second bandage include a bottom face and a top face, wherein the skin fastener is disposed on the bottom face of each of the first bandage and the second bandage, and wherein at least one of the top face of the skin attachment portion of the second bandage, the top face of the skin attachment portion of the first bandage, or the top face of the leg of the first bandage includes a closure adhesive.

* * * * *